(12) United States Patent
Leong et al.

(10) Patent No.: US 7,479,503 B2
(45) Date of Patent: Jan. 20, 2009

(54) PHOTODYNAMIC THERAPY IN SELECTIVE CELL INACTIVATION IN BLOOD AND TREATING IMMUNE DYSFUNCTION DISEASES

(75) Inventors: Simon Leong, Burnaby (CA); Agnes How-Ching Chan, Coquitlam (CA); David William Carey Hunt, Surrey (CA); Julia G. Levy, Vancouver (CA); Martin Renke, Coquitlam (CA); Janice North, Surrey (CA)

(73) Assignees: QLT Inc., Vancouver, British Columbia (CA); The University of British Columbia, Vancouver, British Columbia (CA)

( * ) Notice: Subject to any disclaimer, the term of this patent is extended or adjusted under 35 U.S.C. 154(b) by 128 days.

(21) Appl. No.: 11/048,452

(22) Filed: Jan. 31, 2005

(65) Prior Publication Data

US 2005/0130952 A1    Jun. 16, 2005

Related U.S. Application Data (60) Continuation of application No. 09/583,392, filed on May 31, 2000, now Pat. No. 6,849,058, which is a division of application No. 09/152,993, filed on Sep. 14, 1998, now Pat. No. 6,100,290, which is a continuation of application No. 08/309,509, filed on Sep. 22, 1994, now Pat. No. 5,807,881, which is a continuation-in-part of application No. 07/889,707, filed on May 27, 1992, now Pat. No. 5,776,966.

(51) Int. Cl.
*A61K 31/40*    (2006.01)
*A61N 5/06*    (2006.01)

(52) U.S. Cl. .......................... 514/414; 607/88
(58) Field of Classification Search ............. None
See application file for complete search history.

(56) References Cited

U.S. PATENT DOCUMENTS

| | | | |
|---|---|---|---|
| 4,610,241 A | 9/1986 | Gordon | |
| 4,878,891 A | 11/1989 | Judy | |
| 4,960,408 A | 10/1990 | Klainer | |
| 5,028,594 A | 7/1991 | Carson | |
| 5,036,102 A | 7/1991 | Bachynsky et al. | |
| 5,095,030 A | 3/1992 | Levy | |
| 5,360,734 A | 11/1994 | Chapman | |
| 5,368,841 A | 11/1994 | Trauner | |
| 5,430,051 A | 7/1995 | Aizawa | |
| 5,776,966 A | 7/1998 | North | |
| 5,807,881 A | 9/1998 | Leong et al. | |
| 6,100,290 A | 8/2000 | Levy | |

6,887,862 B2 *   5/2005   Rychnovsky ............... 514/183

FOREIGN PATENT DOCUMENTS

| EP | 392429 | 10/1990 |
|---|---|---|
| WO | WO-93/24127 | 12/1993 |
| WO | WO-94/17797 | 8/1994 |

OTHER PUBLICATIONS

Capra et al., "Significantly Higher Levels of Soluble Interleukin 2 in Patients with Relapsing-Remitting Multiple Sclerosis Compared with Healthy Subjects," Arch. Neurol., vol. 46, p. 254 (1990).
Chowdhary et al., "The Use of Transcutaneous Photodynamic Therapy in the Prevention of Adjuvant-Enhanced Arthritis in MRL/lpr Mice," Clin. Immun. and Immunopath., vol. 72:2, pp. 255-263 (1994).
Edelson, "Photopheresis: A New Therapeutic Concept," Yale J. of Biol. and Med., vol. 62, pp. 565-577 (1989).
Gruner et al., "Inhibition of HLA-DR Antigen Expression and of the Allogeneic Mixed Leukocyte Reaction by Photochemical Treatment," Tissue antigens, 27, 147 and 151-54 (1986).
Levy et al., "Immunomodulatory Effects of PDT Using BPD," Photochem. and Photobiol., vol. 59, pp. 75 (1994).
Matthews et al., "Preliminary Studies of Photoinactivation of Human Immunodeficiency Virus in Blood," Transfusion, 31, 636-41 (1991).
North et al., "Photodynamic Inactivation of Retrovirus by Benzoporphyrin Derivative: a Feline Leukemia Virus Model," Transfusion 32, 121-28 (1992).
North et al., "Photoinactivation of Human Immunodeficiency Virus (HIV) by Benzoporphyrin Derivative," Cell Biochem., Supp., Part E, 85, Abstract Q 545 (1992).
North et al., "Photosensitizers as Virucidal Agents," J. Photochem. Photobiol B.: Biol.,vol. 17, pp. 99-108 (1993).
Obochi et al., "Targeting Activated Lymphocytes with Photodynamic Therapy: Susceptibility of Mitogen-Stimulated Splenic Lymphocytes to Benzoporphyrin Derivative (BPD) Photosensitization," Photochem. and Photobiol., vol. 62:1, pp. 169-175 (1995).
Qin et al., "Enhanced Skin Allograft Survival After Photodynamic Therapy," Transplantation, vol. 56:6, pp. 1481-1486 (1993).
Ratkay et al., "Photodynamic Therapy: A Comparison with Other Immunomodulatory Treatments of Adjuvant-Enhanced Arthritis in MRL-lpr Mice," Clin. Exp. Immunol., vol. 95, pp. 373-377 (1994).
Richter et al., "Non-Oncologic Potentials for Photodynamic Therapy," Proceedings of Photodynamic Therapy of Cancer, Budapest, Hungary (Sep. 1-4, 1993).
Zarling et al., J. Immunol. (1990) 144:2992-2998.
Zuckerman et al., "Treatment of antigen-induced arthritis in rabbits with Dysprosium-165-Ferric Hydroxide Macroaggregates," J. of Orthopaedic Res. 7:50-60 (1989).

* cited by examiner

*Primary Examiner*—Raymond J. Henley, III
(74) *Attorney, Agent, or Firm*—Morrison & Foerster LLP (57)    ABSTRACT

Multiple sclerosis and rheumatoid arthritis can be treated effectively using photodynamic therapy. In this protocol, a photoactive compound is administered, allowed to distribute in the effected subject, and the subject is then irradiated to activate the photoactive compound. Alternatively, the blood of a subject to be treated can be subjected to PDT extracorporeally. In the case of rheumatoid arthritis, localized treatment at the joints may also be employed.

10 Claims, 9 Drawing Sheets

PHOTODYNAMIC THERAPY IN SELECTIVE CELL INACTIVATION IN BLOOD AND TREATING IMMUNE DYSFUNCTION DISEASES

CROSS-REFERENCE TO RELATED APPLICATIONS

This application is a continuation of U.S. Ser. No. 09/583,392, filed May 31, 2000, now U.S. Pat. No. 6,849,058, which is a divisional of U.S. application Ser. No. 09/152,993, filed Sep. 14, 1998, now U.S. Pat. No. 6,100,290, which is a continuation of U.S. application Ser. No. 08/309,509, filed Sep. 22, 1994, now U.S. Pat. No. 5,807,881, which is a continuation-in-part of U.S. Ser. No. 07/889,707 filed 27 May 1992 (now U.S. Pat. No. 5,776,966), the contents of each of which are incorporated herein by reference.

TECHNICAL FIELD

The invention relates to photodynamic methods for selectively depleting blood or bone marrow of cells important in the progress of certain diseases. More specifically, it concerns methods for selectively reducing the population of activated leukocytes in the blood or bone marrow of subjects with immune dysfunctional disorders, such as patients with autoimmune diseases or patients infected with HIV.

Even more specifically, it concerns methods for treating specific autoimmune diseases such as multiple sclerosis and rheumatoid arthritis using photodynamic therapy.

BACKGROUND ART

The immunodisturbances caused by the human immunodeficiency virus have been studied, but the nature of the progress of the disease is still uncertain. However, it has been shown that HIV-infected humans have circulating cytotoxic T-lymphocytes that lyse uninfected $CD4^+$ cells. Zarling et al., *J. Immunol.*, 144:2992 (1990). It is also generally understood that infection with HIV, while depleting the levels of $CD4^+$ cells, enhances the levels of $CD8^+$, $DR^+$, and $IL-2R^+$ leukocytes. $IL-2R^+$ is considered an activation marker, and $DR^+$ is an HLA marker. These may be present on cells with additional markers such as $CD4^+$ and $CD8^+$.

One approach to interfering with the progress of this infection, and the resultant immunosuppression, employs strategies to alter the composition of the blood with respect to various components of the immune system. In one attempt to achieve this, U.S. Pat. No. 4,960,408 discloses a process of treating a subject having AIDS-related complex systemically with psoralen, and then extracorporeally treating the T-lymphocytes with ultraviolet radiation having a wavelength absorbed by the psoralen compound. The irradiated T-cells are then returned to the subject. This treatment apparently enhances the levels of $CD3^+$, $CD4^+$, and $CD8^+$ cells, although not in a uniform fashion.

Photodynamic therapy generally involves the administration of a photoactive agent, permitting the agent to home to cells or tissues whose destruction is sought, and irradiating the cell or tissue with light absorbed by the photoactive agent. In theory, the excited photoactive agent, in decaying to its ground state, generates substances, putatively singlet oxygen, which are toxic to the proximal cells or tissues.

Photodynamic therapy was initially applied to the treatment of tumors in humans and animals. A number of classes of photoactive agents have been described, including psoralens, which are activated by UV light, various hematoporphyrin derivatives which are activated by visible light, and other aromatic systems such as phthalocyanines and modified porphyrins such as chlorins. In addition, U.S. Pat. No. 5,095,030, issued 10 Mar. 1992, which is incorporated herein by reference in its entirety, discloses and claims various wavelength-specific cytotoxic agents that are generically described as "green porphyrins." These compounds are porphyrin derivatives that are modified by a Diels Alder reaction to shift the wavelength of absorption effectively to a longer wavelength. This results in some favorable properties as compared with, for example, hematoporphyrin derivative, when these compounds are employed in photodynamic therapy generally. As described in this patent, these cytotoxic agents, generally called BPDs, absorb visible light at wavelengths which minimize interference by surrounding tissue with the incoming irradiation.

In addition to treatment of tumors and malignancies, photodynamic therapy has been suggested for disrupting atherosclerotic plaques, and for ridding blood supplies of pathogenic agents. In general it was considered that the photoactive agent would be selectively attracted to or retained in the unwanted cells or tissue, as compared to normal cells or tissue and the selectivity of the protocol has been based partly on this feature of the photoactive agents and partly on the focusing of the location at which the visible or UV light is applied.

It has now been found possible to diminish selectively the levels of activated leukocyte subsets that are associated with HIV infection or other immune dysfunctions using a photoactive agent, particularly the green porphyrin compounds described above. This depletion can be effected without side effects on the normally functioning B cell, $CD4^+$ cell, $CD8^+$ cell or NK cell populations. Either leukocytes after separation from red blood cells or whole blood can be treated using the method of the invention.

It has now also been found that two specific autoimmune diseases, multiple sclerosis and rheumatoid arthritis, are verified to respond to photodynamic therapy, not only with respect to use of green porphyrins as photoactive agents, but utilizing photodynamic therapeutic agents generally as well.

DISCLOSURE OF THE INVENTION

The invention provides a method to lower selectively the population of activated leukocytes in subjects showing elevated levels of leukocyte activation markers. The method of the invention involves treating a body fluid, such as bone marrow, blood, or an appropriate fraction thereof, with a specific class of compounds useful in photodynamic therapy, followed by irradiating the blood or fraction with light having at least one wavelength absorbed by the photoactive compound. The treatment can be conducted in vivo, entirely extracorporeally, or partially in vivo and partially ex vivo.

Thus, in one aspect, the invention is directed to a method to reduce selectively the activated leukocyte population in the body fluid of a subject in need of such reduction, which method comprises:

(1) treating the body fluid, or an activated leukocyte-containing fraction thereof, with an effective amount of a photoactive compound, such as a green porphyrin (Gp) compound; and (2) irradiating the treated body fluid with light comprising at least one wavelength absorbed by the photoactive compound.

In another aspect, the invention is directed to a method to treat an HIV-infected patient or other immune dysfunctional patient, which method comprises treating at least a portion of the patient's body fluid, or fraction thereof containing cells to be depleted, with an effective amount of the photoactive compound, followed by irradiation In still other aspects, the invention is directed to leukocyte-activated blood, plasma, or other sub-fraction, that has been depleted of activated leukocytes, HIV-infected cells, or free HIV.

The invention also provides methods for the treatment of multiple sclerosis and rheumatoid arthritis. The methods employ techniques generally used in photodynamic therapy; photoactive compounds are administered and allowed to distribute systemically; the subject is then irradiated with light absorbed by the photoactive compound.

Thus, in one aspect, the invention is directed to a method to ameliorate the symptoms of multiple sclerosis or rheumatoid arthritis which method comprises administering to a subject in need of such amelioration an amount of a photoactive compound effective to distribute in said subject; allowing said distribution to occur; and irradiating the subject with light absorbed by said photoactive compound at an intensity sufficient to activate said photoactive compound to effect its toxicity.

BRIEF DESCRIPTION OF THE DRAWINGS

FIG. 5 shows the generic structures of the various green porphyrins useful in the invention.

FIG. 6 shows the structures of preferred green porphyrins, specifically BPD-MA (FIG. 6A), BPD-MB (FIG. 6B), BPD-DA (FIG. 6C) and BPD-DB (FIG. 6D).

MODES FOR CARRYING OUT THE INVENTION

The methods of the invention also comprise the treatment of a body fluid, such as bone marrow, blood, or appropriate fractions thereof, containing abnormally elevated levels of endogenous, or infected endogenous, cells with a photoactive compound such as green porphyrin compound, followed by irradiation of the body fluid or fraction with light absorbed by the photoactive compound. The method of the invention can be conducted in a variety of protocols. The two most important elements are assuring (1) that the photoactive compound is associated with the cells whose populations are to be diminished and (2) that the photoactive compound associated with these cells is irradiated with the appropriate wavelength. As used herein, "body fluid" refers to body fluids that contain elevated levels of activated leukocytes or other cells, such as HIV-infected cells, to be depleted. Such body fluids typically include bone marrow, blood, and fractions thereof.

While bone marrow can be used as the substrate for the method of the invention, the use of the patient's blood is often more convenient. Thus, in one protocol, whole blood is withdrawn from the subject and treated with a suitable concentration of the photoactive compound for a time period sufficient to permit the compound to be associated with the desired target cells. The whole blood can be irradiated with the appropriate wavelength of light in the extracorporeal container or apparatus, and then the treated and irradiated blood can be returned to the patient.

The blood withdrawn from the patient can also be separated into fractions, typically into a red blood cell fraction and a leukocyte-enriched plasma fraction. The leukocyte-containing plasma is usually treated with a photoactive compound and irradiated before returning the plasma and the red blood cells (if desired) to the patient's body. Of course, the separation into fractions can be conducted at any point during the extracorporeal treatment, so that the photoactive compound could also be added to the whole blood prior to being separated into red blood cells and leukocyte-enriched fractions, and then only the leukocyte-enriched fraction would typically need to be irradiated.

Alternatively, the photoactive compound, or a mixture thereof, can be administered systemically to the patient in suitable formulations, typically by injection, but also by other routes of administration, such as oral administration or transmucosal administration. Once the photoactive compound has been given sufficient time to enter the bloodstream, a suitable radiation source can be applied to the body of the patient. For example, a catheterized fiberoptic device may be inserted into suitable positions in the bloodstream, or an external transdermal light exposure may be employed. The blood or other body fluid can thus be irradiated in vivo.

Suitable subjects for this treatment of the invention include HIV-infected patients who have been shown to have elevated levels of activated leukocytes, such as $DR^+$ and $IL-2R^+$ cells, in their blood. These levels can be diminished selectively by the method of the invention. Other patients who are expected to show elevated levels of these cells include patients showing unwanted immunoactivation generally, such as those subject to graft-versus-host disease or organ transplant rejection as a result, for example, of organ or bone marrow transplantation. For transplantation, either fluids from the donor organ or fluids from the patient recipient may be treated. Other potential subjects are those who show autoimmune conditions such as rheumatoid arthritis, lupus erythematosus, muscular dystrophy, or myasthenia gravis.

Typically, the photoactive agent is administered in such a way as to result in final concentration in the fluid or fluid fraction to be treated of about 0.05-5 µg/ml, preferably about 0.1-1 µg/ml and, most preferably, about 0.5 µg/ml. The treated fluid or fluid fraction is then irradiated with light from any suitable source, such as a laser diode, a light-emitting diode, fiberoptic-conducted laser light, and the like.

Typical wavelengths are in the range of about 600-790 nm, preferably about 630-710 nm and, most preferably, about 790-780 nm. Typical intensities are on the order of about 1-50 J/cm$^2$, preferably about 5-25 J/cm$^2$ and, most preferably, around 8-15 J/cm$^2$. For these intensities, a wavelength range of about 785-695 nm is preferred.

Irradiation is usually continued for about 2-180 minutes, preferably about 15-120 minutes, depending upon the nature and concentration of the photoactive agent, the amount of fluid being treated, the susceptibility of the patient's cells to treatment, the intensity and wavelength of the light, and the method of irradiation (in vivo or ex vivo). Suitable optimization of the concentration of photoactive compound and irradiation parameters is well within ordinary skill.

In one embodiment, the invention provides protocols for ameliorating the symptoms of and generally treating the conditions of multiple sclerosis and rheumatoid arthritis in afflicted subjects. The examples below verify that photodynamic treatment of these conditions is successful. Widely recognized model systems for each of these conditions show successful responses. The parameters described in these illustrations permit designs of successful protocols for human subjects who are to be treated for the conditions that are mimicked by the exemplified models.

In further detail, photoactive agents that are useful in the invention include any compound, preferably an organic compound, that exhibits a selective cytotoxic effect when activated by exposure to electromagnetic radiation, preferably that radiation having a wavelength in the ultraviolet or visible range. It is believed that the activating irradiation excites one or more oxygen atoms in the molecule to form a singlet oxygen state. The excited, singlet oxygen exists only for a short time, but long enough to attack the cell walls of target cells and thus cause the selective necrosis of target, leukocyte cells.

For example, psoralens are activated by UV light, and various hematoporphyrin derivatives are activated upon irradiation with visible light. Other photoactive agents include phthalocyanines and modified porphyrins such as chlorins. Particularly preferred photoactive agents, however, include the green porphyrin compounds ("Gp compounds"), especially the structures shown in FIG. 5, and even more particularly, the structures shown in FIG. 6.

The Gp compounds of the invention are selected from a group of porphyrin derivatives obtained by Diels-Alder reactions of acetylene derivatives with protoporphyrin under conditions which effect a reaction at only one of the two available conjugated, nonaromatic diene structures present in the protoporphyrin-IX ring system (rings A and B). The formulas shown in FIG. 5 represent typical Gp compounds of the invention. These compounds are shown in FIG. 5 with hydrogen occupying the internal ring nitrogens. However, it is understood that the metallated forms, wherein a cation replaces one or both of these hydrogens, can also be employed. It is also understood that these compounds can be labeled either by replacement of one or more of the atoms in the structure by its radioactive form, or by coupling to a radioisotope such as a radioactive metal or, for example, a radioisotope of iodine.

For convenience, an abbreviation of the term hydromonobenzoporphyrin derivative—"BPD"—is generally used to refer to the Gp compounds of formulas 3 and 4 of FIG. 5. BPD's are particularly preferred forms of the Gp compounds of the invention. Furthermore, dimeric forms of Gp compounds can be provided, thus amplifying the ability of the Gp compound to absorb light on a per mole basis. Dimeric and multimeric forms of Gp/porphyrin combinations can also be employed, providing additional absorption wavelengths.

The modified porphyrins referred to as Gp compounds herein can be conjugated to specific ligands reactive with a target, such as receptor-specific ligands, immunoglobulins, or immunospecific portions of immunoglobulins, permitting them to be even more concentrated in a desired target tissue or substances. This conjugation also permits further lowering of the required dose levels, since the material is not then wasted by distribution into other tissues whose destruction, far from being desired, must be avoided.

When the Gp compound is irradiated in situ using light in the visible absorption range, photoactivation results in cytotoxicity to the surrounding tissue. While the absorption spectrum also includes shorter wavelengths, there is an especially useful absorption maximum in the 670-780 nm range.

In general, the position of wavelength absorption is achieved by effectively saturating one of the two π-bonds in one, but not two, of the four pyrrole rings that constitute the typical porphyrin system. In protoporphyrin-IX, two of the pyrroles contain vinyl substitutions, such that the exocyclic π-bond is conjugated to one of the two π-bonds in the ring. A Diels-Alder reaction involving one of these conjugated systems with an acetylene derivative dienophile results in a fused cyclohexadiene—referred to herein as "hydrobenzo"—being fused to the A or B ring, as shown in formulas 1 and 2 of FIG. 5. Rearrangement of the π system in the hexadiene ring results in the compounds of formulas 3 and 4, and reduction provides the compounds of formulas 5 and 6, of FIG. 5. All of these compounds provide a desired bathochromic shift in absorption maximum.

Specific preparations of the Gp compounds particularly useful in the invention are described in detail in the above-referenced U.S. Pat. No. 5,095,030, which is hereby incorporated by reference.

For the compounds shown in FIGS. 5 and 6, generally, $R^1$ and $R^2$ are each, independently, moderate electron-withdrawing substituents, and are, most commonly, carbalkoxy, or alkyl or aryl sulfonyl, or any other activating substituents, which are not sufficiently electron-withdrawing to result in reaction with both the A and B rings rather than reaction with only one, such as cyano or —CONR$^5$ CO— wherein R$^5$ is aryl or alkyl. One of $R^1$ and $R^2$ may optionally be H, while the other is an electron-withdrawing substituent of sufficient strength to facilitate the Diels-Alder reaction.

As used herein, carboxy is, as conventionally defined, —COOH; and carbalkoxy is —COOR wherein R is alkyl; carboxyalkyl refers to the substituent —R'—COOH wherein R' is alkylene; and carbalkoxyalkyl refers to —R'—COOR wherein R' and R are alkylene and alkyl respectively. Alkyl refers to a saturated straight- or branched-chain hydrocarbyl radical of 1-6 carbon atoms such as methyl, n-hexyl, 2-methylpentyl, t-butyl, n-propyl, and so forth. Alkylene is the same as alkyl except that the group is divalent. Aryl or alkyl sulfonyl moieties have the formula SO$_2$R wherein R is alkyl, as defined above, or is aryl wherein aryl is phenyl, optionally substituted with 1-3 substituents independently selected from halo (fluoro, chloro, bromo or iodo), lower alkyl (1-4C) and lower alkoxy (1-4C). In addition, one or both of $R^1$ of $R^2$ can itself be aryl, i.e., phenyl, optionally substituted as defined above.

As shown in FIG. 5, the adduct formed by the reaction of $R^1$—C≡C—$R^2$ with the protoporphyrin-IX ring system (where $R^3$ is a protected form of 2-carboxyethyl, such as 2-carbomethoxyethyl or 2-carboethoxyethyl; and $R^4$ is —CH═CH$_2$) are compounds of formulas 1 and 2. The compound in formula 1 results from addition to the A ring, and formula 2 results from addition to the B ring. In these resulting products of formulas 1 and 2, $R^4$ remains —CH═CH$_2$.

However, this vinyl group is readily derivatized to other embodiments of $R^4$ by addition to, or oxidation of, the vinyl ring substituent of ring B in formula 1 or ring A in formula 2. These addition or oxidation products can be further substituted if the added substituents are functional leaving groups. For example, —Br may be substituted by —OH, —OR (where R is alkyl 1-6C, as above), —$NH_2$, —NHR, —$NR_2$, etc. In a preferred embodiment, however, one of the added substituents is hydrogen, and the other is selected from the group consisting of halo (fluoro, chloro, bromo or iodo), hydroxy, lower alkoxy, amino or amido, sulfhydryl or other organo-sulfide group, or can be itself hydrogen. Addition to the vinyl group does not appreciably change the absorption spectrum of the resulting compound. For example, the product of the Markovnikov addition of water provides a substituent structure analogous to that of the hematoporphyrin ring system at the relevant ring. Thus, the compounds of the invention include various groups as $R^4$, including substituents which provide additional porphyrin or porphyrin-related ring systems, as will be further described below.

$R^3$ in protoporphyrin-IX is 2-carboxyethyl (—$CH_2CH_2COOH$). However, the nature of $R^3$ (unless it contains a π-bond conjugated to a ring π-bond), is ordinarily not relevant to the progress of the Diels-Alder reaction or to the effectiveness and absorption spectrum of the resulting product. $R^3$ can thus be, for example, lower alkyl (1-4C), 1-carboxyalkyl (2-6C), or the esters or amides thereof. The $R^3$ substituent may also be substituted with halogen as defined above, or with other nonreactive substituents. However, particularly convenient starting materials for the Gp compounds of the invention are the naturally-occurring porphyrins, preferably wherein $R^3$ is $CH_2CH_2COOH$ or —$CH_2CHR_2COOR$ where R is alkyl (1-6C).

In the BPD compounds of the invention, it has been found advantageous to hydrolyze or partially hydrolyze the esterified carboxy group in —$CH_2CH_2COOR$. The hydrolysis occurs at a much faster rate than that of the ester groups of $R^1$ and $R^2$, when present, and the solubility and biodistribution characteristics of the resulting compounds are typically more desirable than those of the unhydrolyzed form. Hydrolysis results in the diacid or monoacid products (or their salts).

The hydro-monobenzoporphyrins that result directly from the Diels-Alder reaction described in the above-cited references can also be isomerized to compounds having formulas shown as formulas 3 and 4 of FIG. 5.

The depictions of formulas 3 and 4 in FIG. 5 do not show the relative position of the exocyclic methyl group (ring A of formula 3 and ring B of formula 4) with respect to the $R^2$ substituent. Either isomer is available.

In addition, the Diels-Alder products can be selectively reduced, for example, by treating with hydrogen in the presence of palladium on charcoal, to give the saturated ring analogs, shown as formulas 5 and 6 in FIG. 5, which correspond to the respective Diels-Alder products of rings A and B. These reduced products are generally less preferred embodiments and are generally less useful in the method of the invention than the compounds of formulas 1-4.

The description set forth above with respect to derivitization of compounds of formulas 1 and 2 by converting the remaining vinyl substituent ($R^4$) and with respect to the variability of —$R^3$ applies as well to the compounds of formulas 3, 4, 5 and 6.

The compounds of formulas 3 and 4 (BPD's), and especially those that have hydrolyzed and partially hydrolyzed carbalkoxy groups in $R^3$, are most preferred. Compounds of the invention that contain a —COOH group may be prepared either as the free acid or in the form of salts with organic or inorganic bases.

It will be noted that many of the compounds of FIG. 5 contain at least one chiral center and, therefore, exist as optical isomers. The conjugates and methods of the invention include compounds having both configurations of the chiral carbons, whether the compounds are supplied as isolates of a single stereoisomer or as mixtures of enantiomers and/or diastereomers. Separation of mixtures of diastereomers may be effected by any conventional means. Mixtures of enantiomers may be separated by the usual techniques of reacting with optically active preparations and separating the resulting diastereomers.

It should further be noted that the reaction products may be unseparated mixtures of A and B ring additions, e.g., mixtures of compounds having formulas 1 and 2, or 3 and 4, or 5 and 6. Either the separated forms, i.e., formula 3 alone or 4 alone, or the mixtures in any ratio, may be employed in the methods of therapy and diagnosis set forth herein.

FIG. 6 shows four particularly preferred compounds of the invention, which have not been previously described in the art. These compounds are collectively designated benzoporphyrin derivatives (BPD's) as they are forms of Gp compounds having the formula 3 or 4. These are hydrolyzed or partially hydrolyzed forms of the rearranged products of formulas 3 and 4, wherein one or both of the protected carboxyl groups of $R^3$ are hydrolyzed. The ester groups at $R^1$ and $R^2$ hydrolyze relatively slowly, such that conversion to the forms shown in FIG. 6 is easily effected.

For purposes of this description, $R^3$ is —$CH_2CH_2COOR^{3'}$. As shown in FIG. 6, in a preferred compound of formula BPD-DA, each $R^{3'}$ is H, $R^1$ and $R^2$ are carbalkoxy, and derivatization is at ring A. The preferred BPD-DB compound is the corresponding compound wherein derivatization is at ring B. BPD-MA represents a partially hydrolyzed form of BPD-DA, and BPD-MB, the partially hydrolyzed form of BPD-DB. Thus, in these latter compounds, $R^1$ and $R^2$ are preferably carbalkoxy, one $R^{3'}$ is preferably H and the other $R^{3'}$ is preferably alkyl (1-6C). The compounds of formulas BPD-MA and BPD-MB may be homogeneous, wherein only the C ring carbalkoxyethyl or only the D ring carbalkoxyethyl is hydrolyzed, or may comprise mixtures of the C and D ring-substituent hydrolyzates. In addition, mixtures of any two or more of BPD-MA, -MB, -DA and -DB may be employed in the method of the invention.

Certain other embodiments wherein $R^4$ is other than vinyl, or wherein $R^3$ is a non-native substituent, are also intended to be included in the description of Gp compounds useful in the invention.

Generally, each $R^1$ and $R^2$ is independently selected from the group consisting of carbalkoxy (2-6C), alkyl (1-6C) sulfonyl, aryl (6-10C) sulfonyl, aryl (6-10C); cyano; and —$CONR^5$ CO— wherein $R^5$ is aryl (6-10C) or alkyl (1-6C); each $R^3$ is independently alkyl (1-6C), carboxyalkyl (2-6C), or a salt, amide, ester or acylhydrazone thereof; and $R^4$ is —$CHCH_2$, —$CH_2OR^{4'}$, —CHO, —$COOR^{4'}$, —$CH(OR^{4'})CH_3$, —$CH(OR^{4'})CH_2OR^{4'}$, —$CH(SR^{4'})CH_3$, —$CH(NR^{4'}_2)CH_3$, —$CH(CN)CH_3$, —$CH(COOR^{4'})CH_3$, —$CH(COOCR^{4'})CH_3$, —$CH(halo)CH_3$, or —$CH(halo)CH_2(halo)$, wherein $R^{4'}$ is H or alkyl (1-6C), optionally substituted with a hydrophilic substituent, or wherein $R^4$ is an organic group of <12C resulting from direct or indirect derivatization of vinyl, or wherein $R^4$ is a group containing 1-3 tetrapyrrole-type nuclei of the formula -L-P as herein defined.

Compounds of formulas 3 and 4 of FIG. 5 and mixtures thereof are particularly preferred. Also preferred are those wherein $R^1$ and $R^2$ are the same and are carbalkoxy, especially carboethoxy. Also preferred are those wherein $R^4$ is —CHCH$_2$, —CH(OH)CH$_3$, —CH(halo)CH$_3$, or a group containing 1-3 tetrapyrrole-type nuclei of the formula -L-P (defined below).

As used herein, "tetrapyrrole-type nucleus" represents a four-ring system of the skeleton:

which is abbreviated or a salt, ester, amide or acylhydrazone thereof, which is highly conjugated. It includes the porphyrin system, which is, in effect, a completely conjugated system; the chlorin system, which is, in effect, a dihydro form of the porphyrin; and the reduced chlorin system, which is a tetrahydro form of the completely conjugated system. When "porphyrin" is specified, the completely conjugated system is indicated. A "Gp compound" effectively denotes a dihydro form of the porphyrin system.

In one embodiment, the substituent $R^4$ includes at least one additional tetrapyrrole-type nucleus. The resulting compounds of the invention are dimers or oligomers in which at least one of the tetrapyrrole-type ring systems is a Gp compound. Linkage between the Gp moiety through the position of $R^4$ to an additional tetrapyrrole-type ring system may be through an ether, amine or vinyl linkage. Additional derivatives of porphyrin ring systems that have two available substituent positions (in both A and B rings) corresponding to $R^4$ can also be formed, as further described below.

As stated above, the compounds having the formulas of FIG. 5 include those wherein $R^4$ is formed by addition to the vinyl groups of the initial Gp compound. Thus, $R^4$ can be any substituent that is formed by a facile addition reaction. Therefore, both added substituents can be, for example, —OH or halo, and these substituents can be further substituted. Alternatively, the addition reagent may be of the form HX wherein H is added to the ring-adjacent carbon to provide an $R^4$ of the formula

The vinyl group can also be oxidized to obtain $R^4$ as —CH$_2$OH, —CHO, or —COOH and its salts and esters.

Thus, in general, $R^4$ represents any substituents to which the vinyl group —CH=CH$_2$ is readily converted by cleavage or addition reactions, and further resultants of reacting leaving groups with additional moieties. Typical $R^4$ substituents include: —CH(NH$_2$)CH$_3$, —CH(imidazole)CH$_3$, —CH(OH)CH$_3$, —CHBrCH$_3$, —CH(OCH$_3$)CH$_3$, —CH(pyridinium bromide)CH$_3$, —CH(SH)CH$_3$ and the disulfide thereof, —CHOHCH$_2$OH, —CHO, —COOH and —COOCH$_3$.

When $R^4$ is -L-P, the substituent formula "-L-P" represents a substituent wherein -L- is selected the group consisting of and P is selected from the group consisting of Gp wherein Gp has one of the formulas 1-6 shown in FIG. 5, but lacks $R^4$ and is conjugated to L through the position shown in FIG. 5 as occupied by $R^4$, and a porphyrin of the formula wherein $R^3$ and $R^4$ are as defined above, and the unoccupied bond is then conjugated to L. It is understood that the abbreviation represents a porphyrin of the formula:

wherein each R is independently H or lower alkyl (1-4C).

(It is also understood that when -L- is of the formula (e) or (f), the ring system to which the double bond is attached will have a resonance system corresponding to in the ring to which the double bond is attached, as shown.)

Preparation of the Dimers and Oligomers

The dimers and oligomeric compounds of the invention can be prepared using reactions analogous to those for dimerization and oligomerization of porphyrins per se. The Gp compounds or green porphyrin/porphyrin linkages can be made directly, or porphyrins may be conjugated first, followed by a Diels-Alder reaction of either or both terminal porphyrins for conversion to the corresponding Gp compound.

For treating subjects, especially human subjects, who exhibit symptomologies of multiple sclerosis, a photoactive compound, such as green porphyrin compounds or mixtures thereof, is administered systemically, typically by injection. Injection may be intramuscular, intravenous, subcutaneous, intraperitoneal, or any other recognized route of injection. Other means of systemic administration may also be used. For example, transmucosal administration is effected using excipients such as bile salts or fusidic acid salts. Transdermal and oral routes of administration with appropriate formulations are also available. However, injection, especially injection in the form of a liposomal composition, is preferred.

The amount of photoactive compound to be administered depends on the condition of the patient, the judgment of the physician, the stage of the condition, the route of administration, and, of course, the nature of the photoactive agent. For typical hematoporphyrin derivative-type photoactive agents, in particular porfimer sodium, suitable dosage ranges are of the order of 0.01-30 mg, preferably 0.1-5 mg, per kilogram body weight. For representative green porphyrins, such as BPD-MA, typical dosage ranges are 0.005-5 mg, preferably 0.05-1 mg, per kilogram body weight. These dosage ranges are merely typical and not intended to define outer limits. The two photoactive compounds exemplified are nontoxic and can be tolerated well by subjects.

The formulation employed will vary with the mode of administration—for injection, typical preparations contain physiological saline, buffers, and, other excipients. Liposomes or other lipocomplexes are preferred. Suitable formulations for administration of therapeutic agents in general may be found in Remington's Pharmaceutical Sciences, latest edition, Mack Publishing Company, Easton, Pa.

Administration of the photoactive agent may begin as soon as the condition of multiple sclerosis in the subject is verified. Typically, in response to early symptomology such as tingling in the extremities, the subject is diagnosed through a CAT scan and verified to have this condition. Either a single administration or repeated administrations prior to a particular treatment with light may be used. If repeated administrations are employed, they are generally within approximately 30 minutes of each other so as to permit the repeated administrations to behave collectively as at time zero. However, a single administration is preferred.

The photoactive agent is then permitted to distribute in the subject. By "distribute" is meant that sufficient time is permitted to elapse so that the photoactive agent is no longer localized at the site of administration. Since transdermal illumination often be used, it is preferable to wait until the photoactive agent has mostly cleared the skin but to administer the light treatment before the systemic levels of the photoactive compound have been cleared.

As explained above, while it was originally believed that the photoactive agent should be permitted to clear normal tissue and to accumulate in unwanted cells or tissues prior to irradiation, it has been found, as described in U.S. Ser. No. 07/979,546, filed Nov. 20, 1992, now abandoned, incorporated herein by reference, that shorter intervals are sufficient to permit sufficient distribution to effect photodynamic therapy. Thus, in the present application, the time required for the photoactive agent to distribute in the subject is expected to be about 4-7 hours. In general, the photoactive agent increases in concentration in the skin over a period of 30 minutes-2½ hours and reaches a maximum at about 3 hours. Substantial amounts clear the system by 7 hours after administration. Thus, an ideal time for irradiation with light is in the range of 4-7 hours after administration of the drug.

After distribution has occurred, the subject is irradiated with light which comprises wavelengths that are absorbed by the photoactive agent. The patient may be subjected to transdermal radiation. The absorption spectra of the photoactive agents will be informative as to which wavelengths to employ. The intensity required depends on the width of the wavelength band but typical intensities are of the order of 1-500 J/cm$^2$, preferably about 5-250 J/cm$^2$ and most preferably around 10-50 J/cm$^2$. The irradiation is continued for about 2-180 minutes, preferably about 15-120 minutes depending on the nature and concentration in the blood stream of the photoactive agent and the susceptibility to the treatment.

Generally, subjects who show evidence of multiple sclerosis, and other immune dysfunctions, may be treated once or several times with a photodynamic treatment which consists of administration of the photoactive agent, allowing for distribution of the photoactive agent, and irradiating the subject. The subjects are monitored for the effects of photodynamic therapy on the condition and re-subjected to this therapy when needed. When the monitoring is multiple sclerosis, such monitoring is most conveniently conducted using CAT scans.

As an alternative to administering the photoactive agent systemically and providing transdermal irradiation, the blood stream of the patient can be treated extracorporeally. Either whole blood or a suitable fraction, e.g., the plasma, can be treated. In that event, the photoactive agent is administered so as to result in a final concentration in the fluid to be treated appropriate to the photoactive agent used. For BPD-MA, for example, typical concentrations are about 0.05-5 µg/ml, preferably about 0.1-1 µg/ml and most preferably about 0.5 µg/ml. Under these circumstances, no time for distribution of the photoactive agent is required. The fluid is then irradiated with light from any suitable source such as laser diode, a light-emitting diode, fiber-optic conducted laser light and the like. The wavelength, as above, depends on the absorption spectrum of the photoactive agent and the light intensities are as described above. Generally, irradiation is continued for time periods similar to those for transdermal radiation.

As stated above, only the relevant fraction of the blood need be treated. Fractionation can be conducted at any stage of the process. Thus, the photoactive agent could be added to whole blood, the blood then fractionated, and the relevant fraction irradiated. Alternatively, the blood could be fractionated first, the photoactive compound then added, and that fraction treated with light. Either the fraction or restored whole blood can be returned to the patient. In general, the suitable fraction will contain the white blood cells. In a typical procedure, therefore, only the plasma need be treated and returned.

Thus, a typical protocol for treatment of a subject with multiple sclerosis would comprise the following steps: about 35 mg BPD-MA formulated as a liposomal preparation is injected i.v. to a subject exhibiting the symptoms of multiple sclerosis. The subject is then irradiated at one of two time points: "early treatment" is performed at about 0.5 to 2.5 hours and "late treatment" is performed at about 5-7 hours post-injection. The subject is irradiated with red light at a wavelength of 690 nm.+−0.10 nm for about 30 minutes. For early treatment the intensity is between about 10-50 J/cm$^2$, more preferably about 15-25 J/cm$^2$, most preferably about 20 J/cm$^2$. For late treatment, the intensity is between about 150-250 J/cm$^2$, more preferably about 200 J/cm$^2$. The patient is then monitored for the results of the photodynamic therapy.

For treatment of rheumatoid arthritis, similar parameters are significant. The model in Example 2 below is predictive of the behavior of rheumatoid arthritis in humans. In connection with this condition, either systemic or localized treatment may be employed. Systemic treatment generally is productive in attacking the disease as a whole, whereas local treatment of the joints addresses the symptoms.

For systemic treatment, typically injection is employed. Injection may be intramuscular, intravenous, subcutaneous, intraperitoneal, or any other recognized route of injection. Other means of systemic administration including oral, transmucosal and transdermal as described above, can be employed. For local administration, the photoactive compound can be injected directed into the affected joints. The amount of photoactive compound to be administered depends on the condition of the patient, the judgment of the physician, the stage of the condition, the route of administration, and, of course, the nature of the photoactive agent. For typical hematoporphyrin derivative-type photoactive agents, in particular porfimer sodium, and for representative green porphyrins, such as BPD-MA, suitable dosage ranges are of the same order as described above for treatment of multiple sclerosis. The formulation employed will vary with the mode of administration—for injection, typical preparations contain physiological saline, buffers, and when injection is employed as a route of administration, formulations which include liposomes or other lipocomplexes are preferred. Suitable formulations for administration of these therapeutic agents may be found in Remington's Pharmaceutical Sciences, latest edition, Mack Publishing Company, Easton, Pa.

Administration of the photoactive agent may begin as soon as the condition of rheumatoid arthritis in the subject is verified. As above, either single administration or repeated administrations prior to a particular treatment with light may be used. In general, for systemic administration, a single administration of the photoactive agent is preferred. For local injection, repeated administration of a photoactive agent at closely proximal times may be required.

If systemic administration is employed, the photoactive agent is then permitted to distribute in the subject. By "distribute" is meant that sufficient time is permitted to elapse so that the photoactive agent is no longer localized at the site of administration. As explained above, while it was originally believed that the photoactive agent should be permitted to clear normal tissue and to accumulate in unwanted cells or tissues prior to irradiation, it has been found, as described in U.S. Ser. No. 07/979,546, filed Nov. 20, 1992, now abandoned incorporated herein by reference, that shorter intervals are sufficient to permit sufficient distribution to effect photodynamic therapy. If transdermal irradiation is utilized, the time periods are as described above for the treatment of multiple sclerosis. If localized irradiation is employed directly to the joints, for example, through laser-connected fiber optic inserted into the joint per se, it is only necessary to allow adequate time for the photoactive agent to obtain sufficient concentration at the joint. This is generally after about 30 minutes, although other times may be employed as well. If local administration of the photoactive agent has been used, of course, administration of light can be almost immediate.

As described above for treatment of multiple sclerosis, extracorporeal treatment of the blood stream can also be employed. The conditions described above are applicable here as well.

At the appropriate time, after distribution has occurred, the subject is irradiated with light which comprises wavelengths that are absorbed by the photoactive agent. The absorption spectra of the photoactive agents will be informative as to which wavelengths to employ. For transdermal irradiation, the intensity and time periods described above apply. For localized irradiation of the joints, the irradiation may either be transdermal in the case of smaller joints or may be conducted invasively using fiberoptics in the case of larger ones. The intensities and times are similar to those for transdermal irradiation.

For extracorporeal treatment, the parameters are as described above in the case of multiple sclerosis.

Thus, a typical protocol for treatment of a subject with rheumatoid arthritis would comprise the following steps: about 3 mg of BPD-MA formulated in a liposomal formulation is injected directly into the joint of a subject exhibiting the symptoms of rheumatoid arthritis. Immediately thereafter, the joint is irradiated with 690 nm±10 nm light at 25 J/cm$^2$ for about 15 min. The patient is then monitored for the results of the photodynamic therapy.

The following examples are intended to illustrate but not to limit the invention.

EXAMPLE 1

Response of Various Leukocytes to BPD and Irradiation

Blood was withdrawn from two patients who were shown to be infected with HIV. Whole blood from each patient was brought to varying concentration levels with BPD-MA and then irradiated with light at 10.8 J/cm2 using 690 nm light emitted from LEDs over a four-minute time period. The populations of various subsets of T-cells were evaluated by flow cytometry in comparison with untreated controls. The percentage of cells present was evaluated as a percentage of control and then plotted as a function of BPD-MA concentration.

Figure 1A:
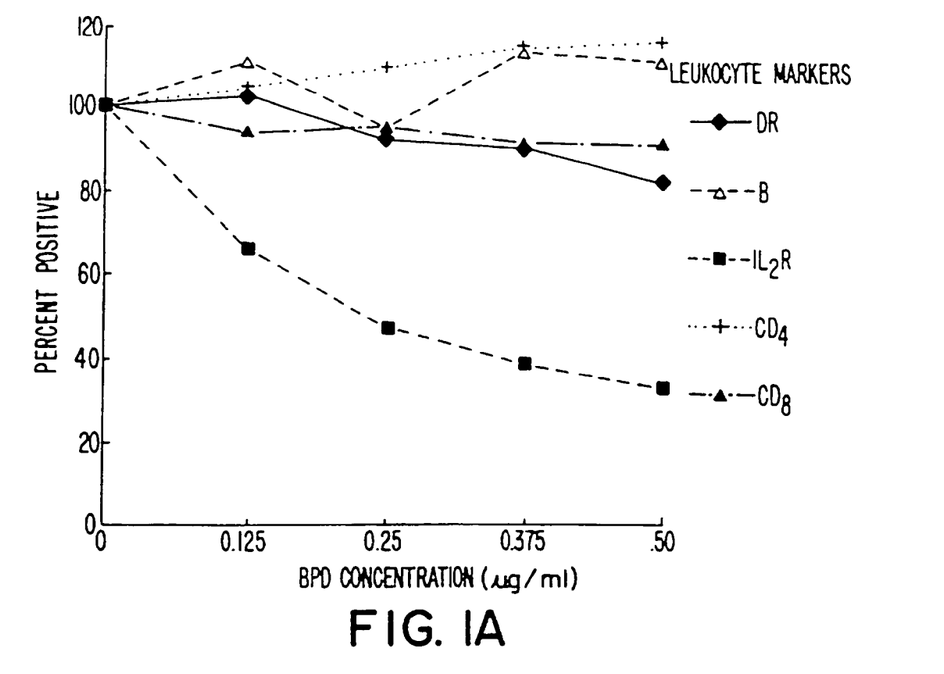
FIGS. 1A and 1B show the effect of Gp and irradiation on various subsets of leukocytes having various markers including B cells, $CD4^+$ cells, $CD8^+$ cells, $DR^+$ cells, and $IL-2R^+$ cells in blood from two HIV-infected patients.
Figure 1B:
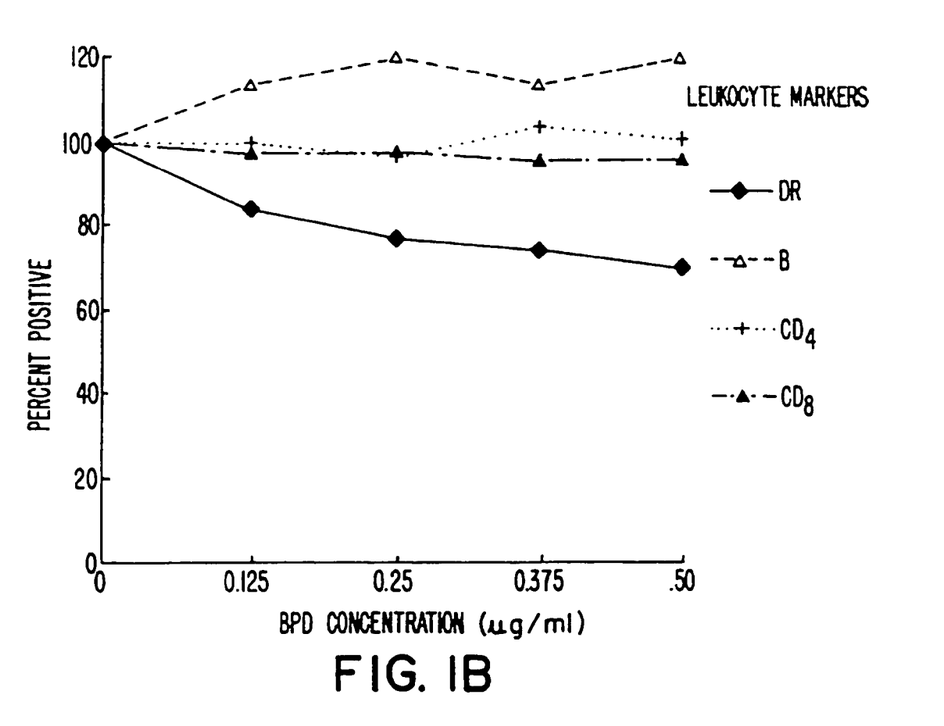

The results obtained are shown in FIGS. 1A and 1B. As indicated, most cell populations remained relatively constant, including B-cells and CD4$^+$ cells. Slight decreases were shown in CD8$^+$ cells and DR$^+$ cells. IL-2R$^+$ cells showed a dramatic decrease for the patient results plotted in FIG. 1A, and this decrease was dependent on the dose of BPD-MA being used.

As shown in FIG. 1A, although IL-2R$^+$ cells were dramatically decreased, significant decreases for CD8$^+$ cells and DR$^+$ cells were also observed. The effect on DR$^+$ cells was more dramatically shown for the second patient in FIG. 1B.

Figure 2:
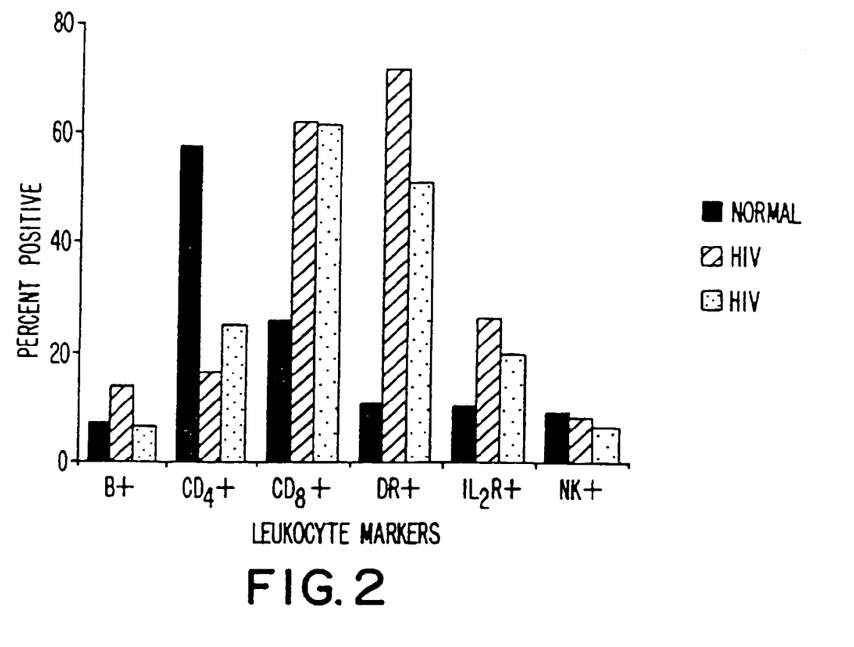
FIG. 2 shows the relative concentrations of the subsets of leukocytes in blood from a normal donor and from two HIV-infected patients.

Similar studies were conducted with a constant concentration of BPD-MA (0.5 μg/ml), using as subjects one normal individual and two HIV patients. FIG. 2 shows the sub-populations of leukocytes in untreated blood obtained from these three donors. As shown in FIG. 2, B-cells and natural killer cells occurred at roughly the same levels in the normal and HIV subjects. However, ARC patients consistently showed diminished levels of CD4$^+$ and elevated levels of CD8$^+$, DR$^+$ and IL-2R$^+$.

Figure 3A:
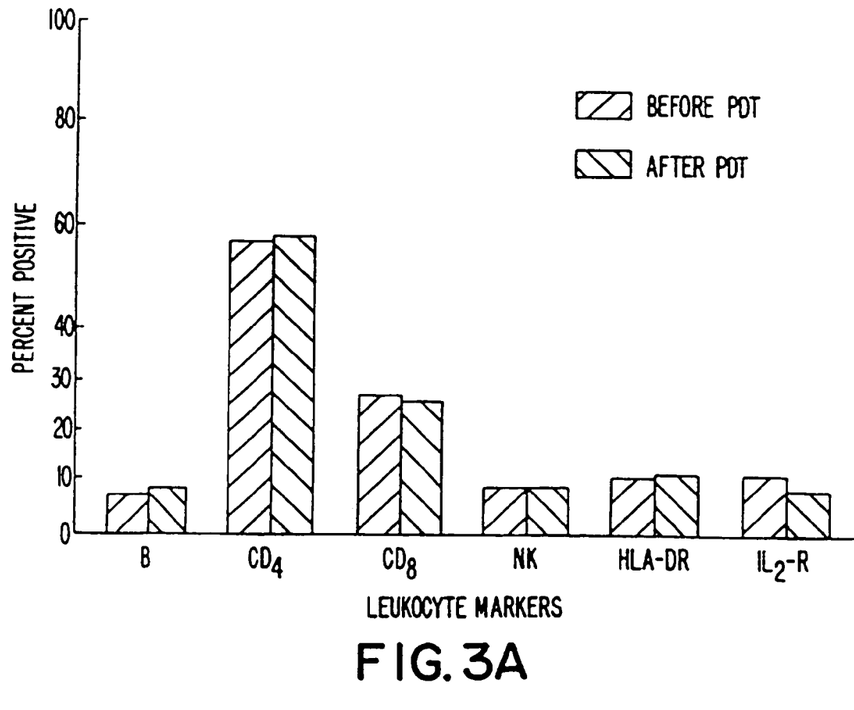
FIGS. 3A and 3B show the relative concentrations of subsets of leukocytes in blood from a normal donor and an HIV donor, respectively, before and after treatment with BPD and irradiation.
Figure 3B:
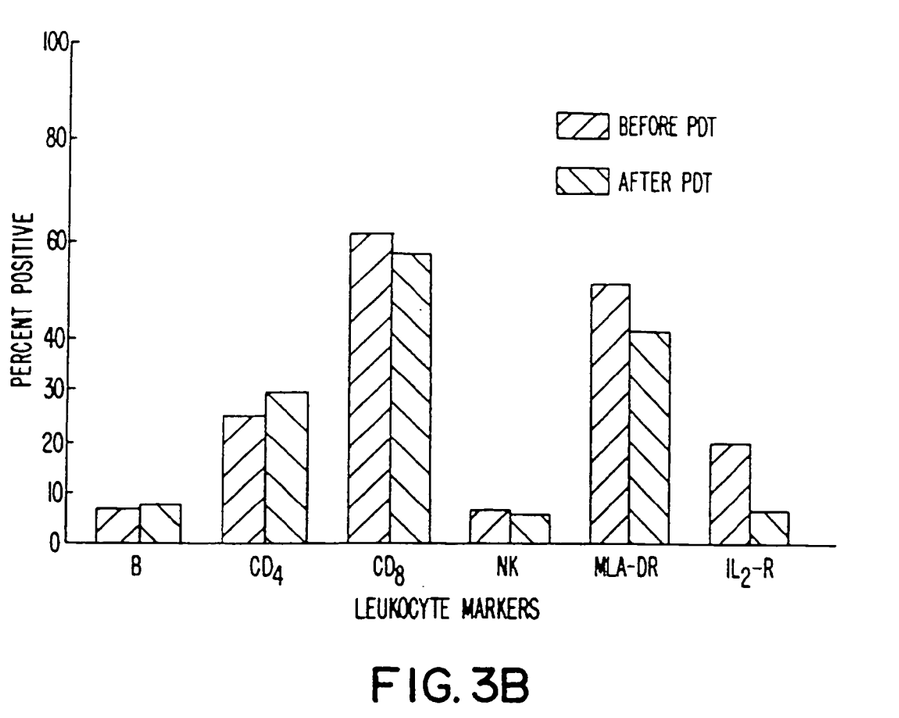
Figure 3C:
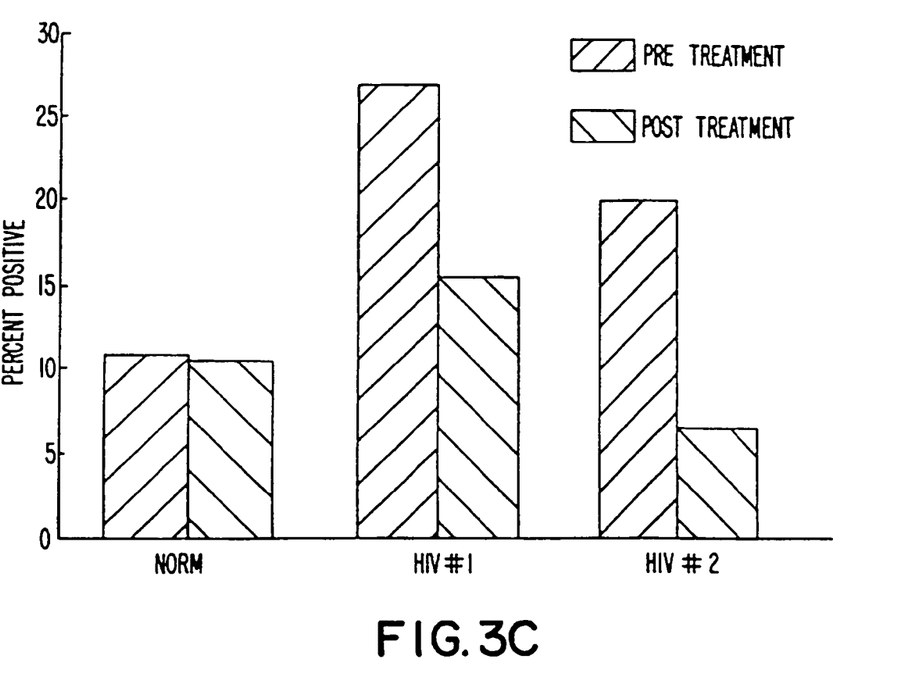
FIG. 3C shows the levels of $IL-2R^+$ cells, specifically before and after treatment with BPD and irradiation, both in normal and HIV-infected subjects.

FIGS. 3A, 3B, and 3C show the effects of the treatment of the invention. As shown in FIG. 3A, treatment of leukocyte sub-populations in normal blood had little effect on any of the populations shown. FIG. 3B shows that, when HIV-infected blood was subjected to this treatment, there was a slight diminution in CD8$^+$, a slight diminution in DR$^+$, and a significant decrease in IL-2R$^+$ cells. FIG. 3C shows these results specifically for IL-2R$^+$ cells, both for normal subjects and for two HIV-infected subjects. Again, the dramatic decrease was observed.

Thus, after treatment with 0.5 μg/ml BPD for four minutes in the presence of 10.8 J/cm$^2$ of light centered at 690 nm, the cell populations of all of the cell types in the normal subject, and all cell types except for IL-2R$^+$ in the HIV subjects, remained relatively constant. DR$^+$ and CD8$^+$ cells were slightly decreased. The BPD/light treatment seemed to have little or no effect on most subclasses of leukocytes. However, the elevated levels of IL-2R$^+$ cells were restored to normal.

EXAMPLE 2

Figure 4:
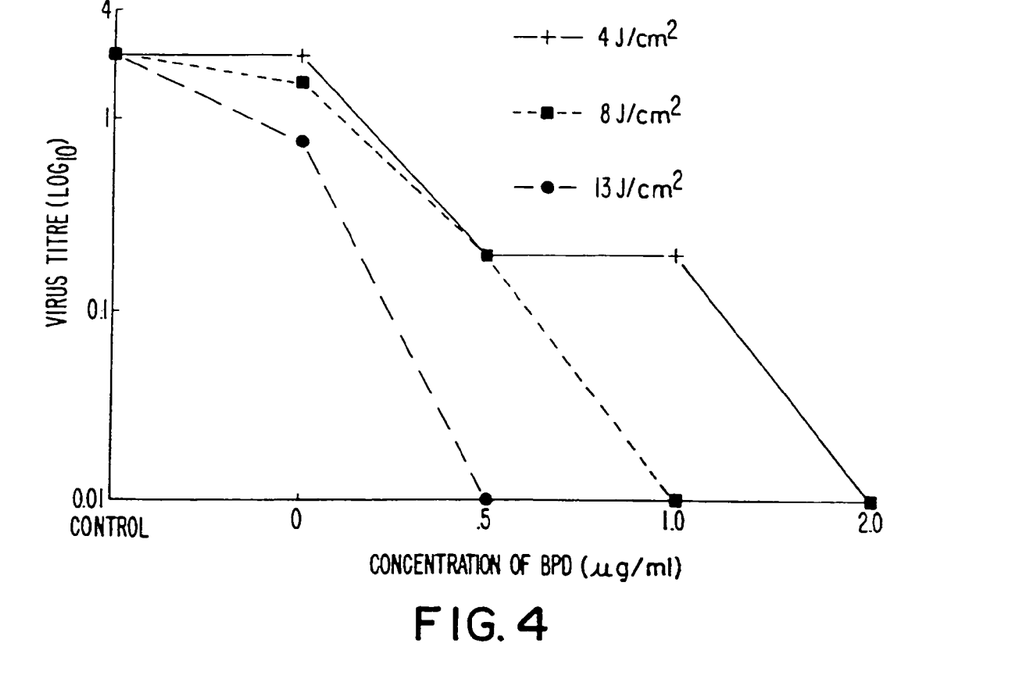
FIG. 4 shows the inactivation of cell-associated HIV by treatment with BPD and irradiation.
Figure 5A:
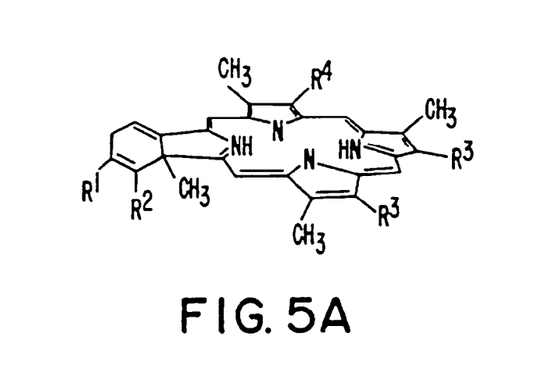
FIG. 5A shows the structure of formula 1.
Figure 5B:
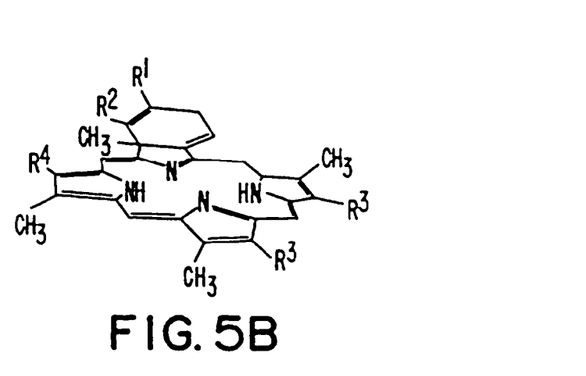
FIG. 5B shows structure formula 2.
Figure 5C:
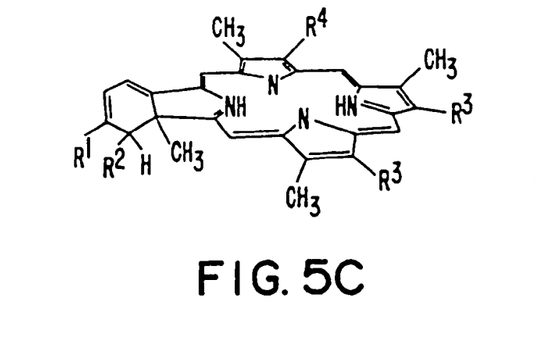
FIG. 5C shows the structure of formula 3.
Figure 5D:
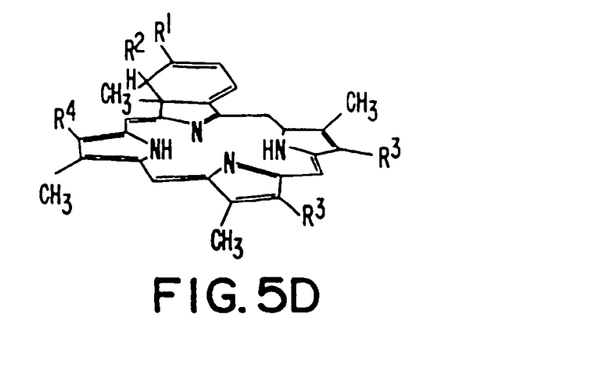
FIG. 5D shows the structure of formula 4.
Figure 5E:
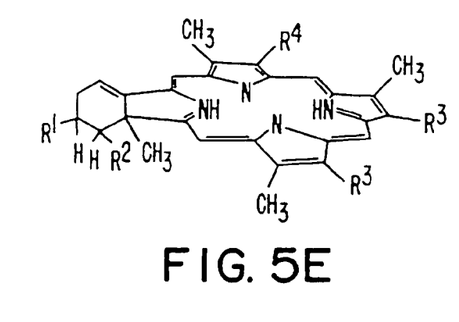
FIG. 5E shows the structure of formula 5.
Figure 5F:
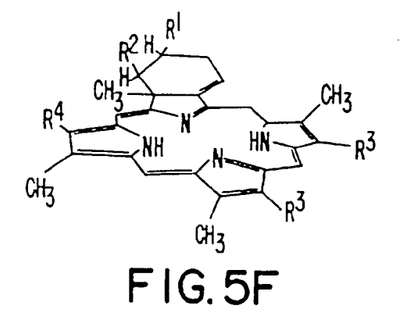
FIG. 5F shows the structure of formula 6.
Figure 6A:
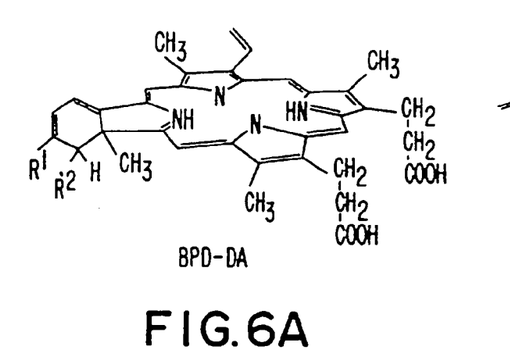
Figure 6B:
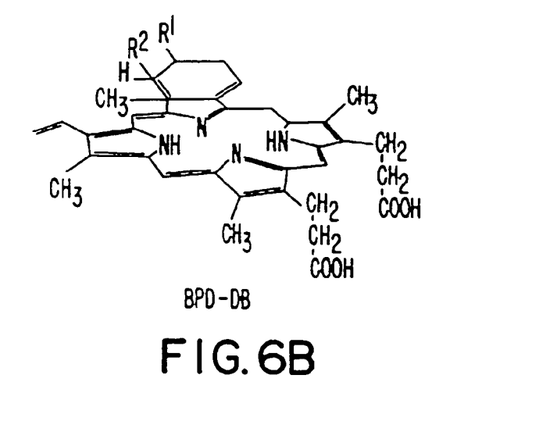
Figure 6C:
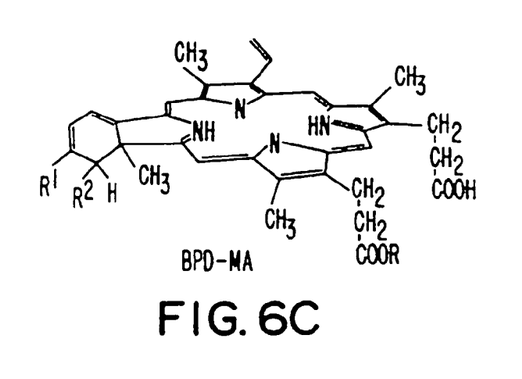
Figure 6D:
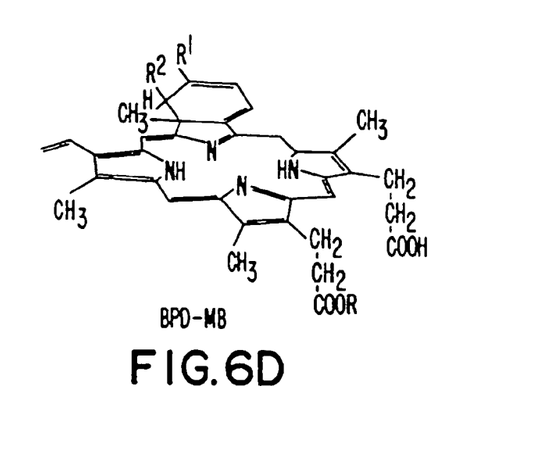

Whole human blood from an HIV patient was also subjected to treatment using various concentrations of BPD and various light intensities in a protocol similar to that set forth in Example 1. The effect on inactivation of cell-associated HIV was tested. The results obtained are shown in FIG. 4. As shown, intensities of 13 J/cm$^2$ produced a dramatic inactivation of the virus at BPD concentrations of about 0.5 μg/ml or less. Lower intensities of radiation required higher concentrations of BPD to inactivate the virus completely.

EXAMPLE 3

The ability to inactivate free HIV (LAV-1 strain) in tissue culture of CEM cells was also tested. In the assay, LAV-1 stock was diluted into the tissue culture medium, and BPD was added at a concentration of either 0.25 μg/ml or 0.5 μg/ml. The media were incubated for one hour and exposed to three minutes of irradiation centered at 690 nm and at an intensity of 10.8 J/cm$^2$. The media were then added to CEM cells, and the cells were assayed, using a standard p24 assay, after six days of culturing. The results were read in terms of pg/ml.

The results obtained are summarized below in Table 1. As shown, at dilutions of LAV that provided high levels of p24, treatment with BPD, a BPD concentration of either 0.25 μg/ml or 0.5 μg/ml was capable of lowering substantially the level of p24 determined.

TABLE 1

| LAV-1 DILUTION | TREATMENT No Drug no light | TREATMENT .25 μg BPD 3 min | TREATMENT .5 μg BPD 3 min |
| --- | --- | --- | --- |
| $10^{-2}$ | >616 | 23.2 | 14.2 |
| $3 \times 10^{-2}$ | >616 | 18.2 | 14.5 |
| $5 \times 10^{-2}$ | >616 | 15.1 | 11.4 |
| $7 \times 10^{-2}$ | >616 | 8.9 | 7.6 |
| $9 \times 10^{-2}$ | >616 | 7.6 | 5.4 |
| $10^{-3}$ | >616 | 4.5 | 7.0 |
| $3 \times 10^{-3}$ | >616 | 5.1 | 3.2 |
| $5 \times 10^{-3}$ | >616 | 4.5 | 3.9 |
| $7 \times 10^{-3}$ | >616 | 3.9 | 2.0 |
| $9 \times 10^{-3}$ | >616 | 5.4 | 2.3 |
| $10^{-4}$ | >616 | 2.0 | 4.2 |
| $3 \times 10^{-4}$ | >616 | 3.6 | 2.0 |
| $5 \times 10^{-4}$ | >616 | 2.9 | 2.3 |
| $7 \times 10^{-4}$ | >616 | 3.2 | — |
| $9 \times 10^{-4}$ | 2.6 | 2.6 | — |

EXAMPLE 4

Treatment of Experimental Allergic Encephalomyelitis

Experimental allergic encephalomyelitis (EAE) is generally recognized as a valid model for MS. See, for example, Steinman, L. Springer Seminars Immunopathol (1992) 14:79-93. In mice, it is triggered by injection with myelin basic protein (MBP) and is mediated by MBP-specific T cells which attach to the myelin sheath of the central nervous system, infiltrate the area, and cause progressive paralysis of the hind limbs (Bernard, C. C. A., et al., *J Immunol* (1975) 114:1537). The present inventors have developed an improvement on this model whereby MBP-primed splenocytes or lymphocytes from PL mice, a strain which provides a monoclonal response to MPB, are cultured in vitro with MBP and IL-2 and then transferred to naive recipients. Transfer of these cultured cells causes disease in 100% of the recipients in almost synchronous manner.

In a preliminary study, the cells to be transferred were preincubated with 100 ng/ml of BPD verteporfin for 60 min in the dark, washed, and resuspended in 200 μl of medium containing 5% FCS. Fifty μl of 40 μg/ml BPD in a liposomal preparation was added to the cells and the mixture was injected i.v. into naive PL recipients. The animals were given transdermal irradiation using a box containing narrow spectrum light emitting diodes (690 nm±10 nm) for 20 min (15 J/cm$^2$).

Figure 7:
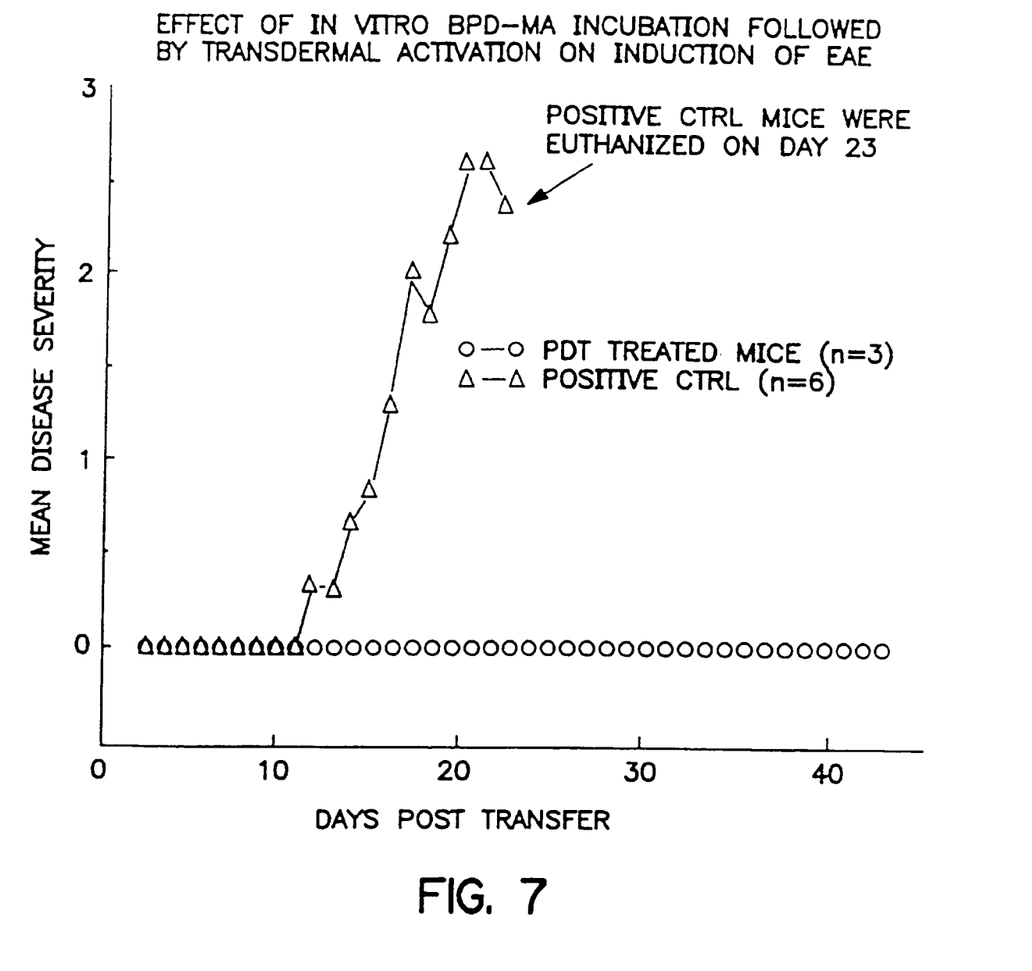
FIG. 7 is a graph contrasting the disease severity in PDT-treated and untreated mice after induction of experimental allergic encephalomyelitis (EAE).

FIG. 7 shows that the animals injected with cells treated with BPD did not develop EAE whereas controls receiving cells did develop this condition.

Figure 8:
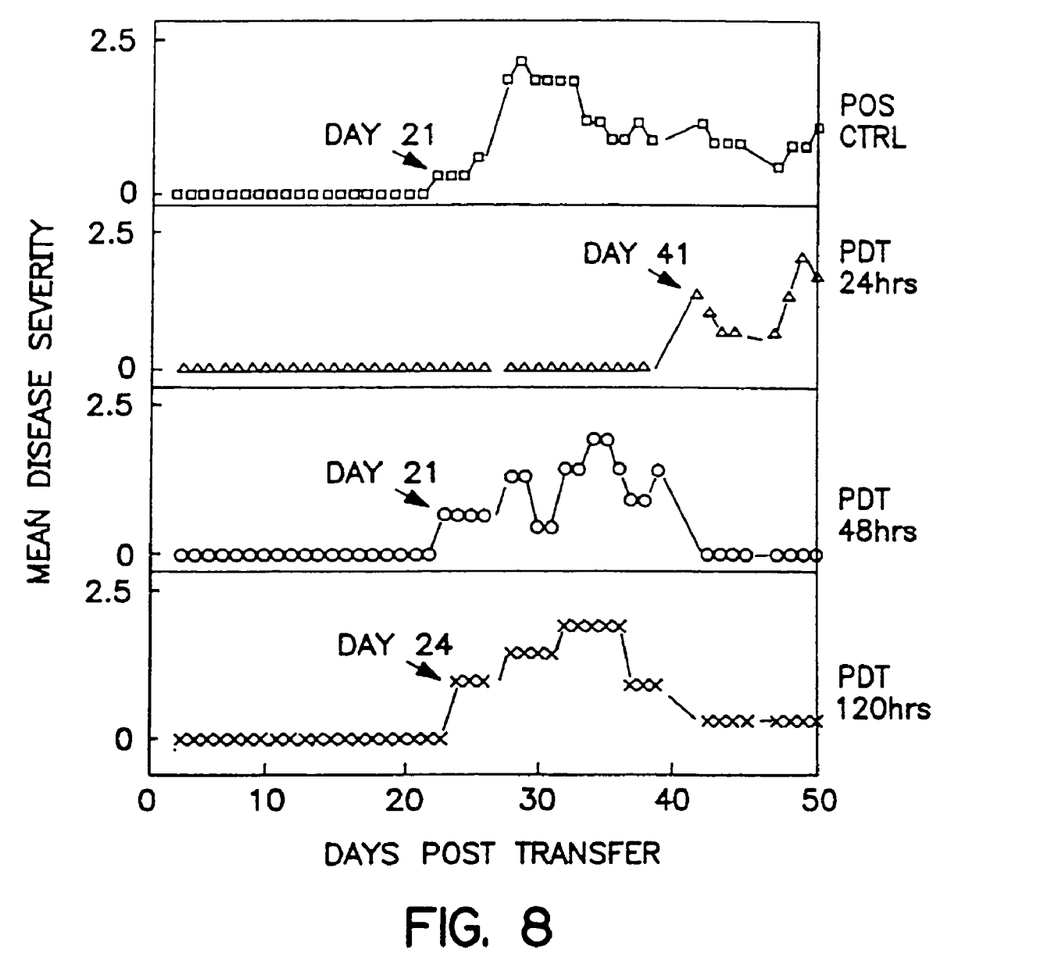
FIG. 8 is a graph showing the effect of transdermal PDT on induction of EAE in mice.

In an additional set of experiments, mice that had been injected with the above-described cultured lymphocytes were administered 1 mg/kg of BPD in a liposomal formulation immediately after the injection of the lymphocytes. The treated mice were housed in the dark for 60 min before exposure to light as described above. The photodynamic therapy protocol (i.e., injection of the BPD-MA followed 60 minutes later by exposure to light) was administered, in separate experimental groups, at various times after injection of the cultured lymphocytes. The results in FIG. 8 show that administration of the PDT treatment within 24 hours delayed the onset of EAE from day 21 to day 41. However, delaying treatment for 48 hours resulted in treatment being ineffective.

In an additional experiment, PDT was administered to the animals 24 hours before the lymphoid cells were injected. This protocol was also protective with respect to EAE.

EXAMPLE 5

Treatment of Collagen-Induced Arthritis

Collagen-induced arthritis is a recognized experimental model for the study of rheumatoid arthritis.

CIA is induced in DBA/1 mice by subcutaneous injection with bovine type II collagen. In the present model, two injections of collagen were administered, the first on day 0 and the second on day 21 (Trentham, D. E. et al., *J Exp Med* (1977) 146:857; Courtenay, J. S. et al., *Nature* (1980) 283:665).

Figure 9:
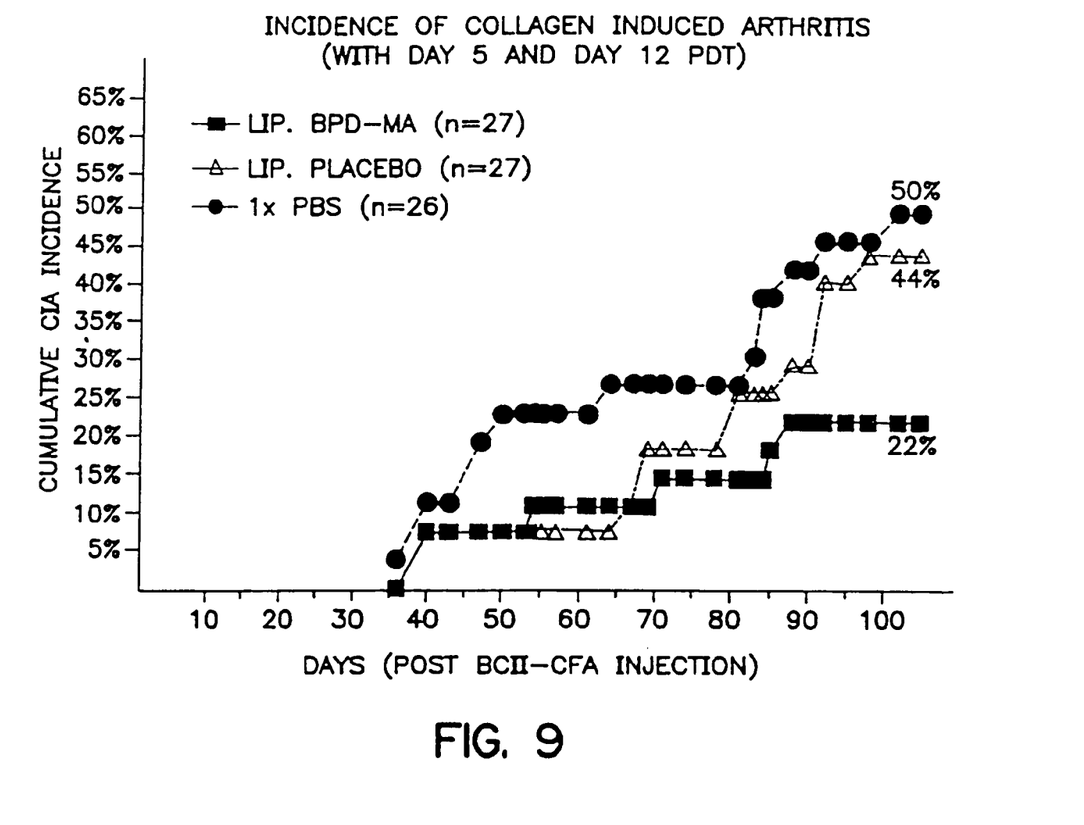
FIG. 9 is a graph showing the effect of PDT using liposomal BPD-MA on the incidence of collagen-induced arthritis in mice.

In one PDT regimen, mice were injected with 1 mg/kg of liposomal BPD i.v. on days 5 and 12, kept in the dark for 60 min after injection and then exposed to transdermal light treatment in a box which provided narrow irradiation by narrow spectrum light-emitting diodes (690 nm±10 nm) for 20 min (15 J/cm$^2$). As shown in FIG. 9, mice administered the PDT treatment showed a substantially lower incidence of CIA than did controls.

Figure 10:
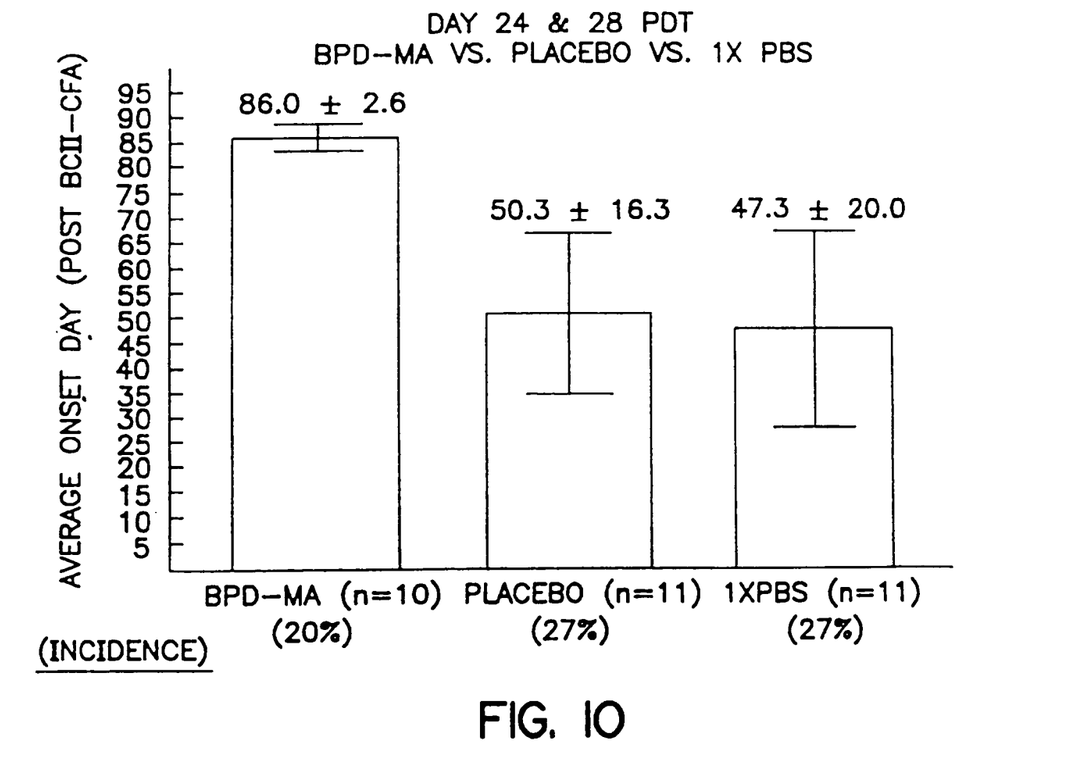
FIG. 10 shows results of similar treatment conducted at a different time in the model.

In a second regimen, the above PDT treatment as described was given on days 24 and 28; as shown in FIG. 10, disease onset was significantly delayed in the treated mice.

The invention claimed is:

1. A method for ameliorating the physiological effects of multiple sclerosis, which method comprises
    a) administering to a subject in need of such amelioration an amount of a photoactive compound effective to distribute in said subject;
    b) allowing said distribution to occur; and
    c) irradiating the subject with light absorbed by said photoactive compound at an intensity sufficient to activate said photoactive compound to effect its toxicity.

2. The method of claim 1 wherein said photoactive compound is a porphyrin-based compound not conjugated to a specific ligand reactive with a target.

3. The method of claim 2, wherein said compound is a green porphyrin.

4. The method of claim 3, wherein said green porphyrin is BPD-MA.

5. The method of claim 1, wherein said subject is a human.

6. The method of claim 1, wherein said photoactive compound is not conjugated to a specific ligand reactive with a target.

7. The method of claim 3, wherein said green porphyrin (Gp) has a formula selected from the group consisting of -continued

4

5

6 wherein:
each of $R^1$ and $R^2$ is independently carbalkoxy, alkyl or aryl sulfonyl, aryl, cyano, or —$CONR^5CO$— where $R^5$ is alkyl or aryl;
each $R^3$ is independently lower alkyl, carboxyalkyl or a salt, ester, amide or acylhydrazone thereof; and
$R^4$ is —$CH=CH_2$, —$CH_2OR^{4'}$, —CHO, —$COOR^{4'}$, —$CH(OR^{4'})CH_3$, —$CH(OR^{4'})CH_2OR^{4'}$, —$CH(SR^{4'})CH_3$, —$CH(NR^{4'}{}_2)CH_3$, —$CH(CN)CH_3$, —$CH(COOR^{4'})CH_3$, —$CH(COOCR^{4'})CH_3$, —$CH(halo)CH_3$, or —$CH(halo)CH_2(halo)$, wherein $R^{4'}$ is H, alkyl, an organic group of less than 12C resulting from direct or indirect derivatization of vinyl, or a group containing 1-3 tetrapyrrole-type nuclei of the formula -L-P wherein:
L is selected from the group consisting of:

(a)  —CH—O—CH—,
         |         |
        CH₃     CH₃

(b)  —CHNHCH—,
         |         |
        CH₃     CH₃

(c)  —CH=CH—CH—,
                         |
                        CH₃

(d)  —CH—CH=CH—,
         |
        CH₃

(e)  =CH—CO—CH—, and
                        |
                       CH₃

(f)  —CH—CO—CH=; and
         |
        CH₃

P has a structure selected from the group consisting of Gp where Gp is of the formulae 1-6, but lacks $R^4$ and is conjugated to L through the position shown in formula 1-6 as occupied by $R^4$, and a porphyrin of the formula wherein R is H or alkyl, $R^3$ and $R^4$ are as defined above, and the unoccupied bond is conjugated to L.

8. The method of claim 7, wherein $R^1$ and $R^2$ are carbomethoxy or carboethoxy.

9. The method of claim 8, wherein each $R^3$ is —$CH_2CH_2COOH$ or a salt, amide, ester or acyl hydrazone thereof.

10. The method of claim 2, wherein said compound is porfimer sodium.

* * * * *